United States Patent [19]

Armentano et al.

[11] Patent Number: 5,707,618
[45] Date of Patent: Jan. 13, 1998

[54] ADENOVIRUS VECTORS FOR GENE THERAPY

[75] Inventors: Donna Armentano, Belmont; Helen Romanczuk, Westboro; Samuel Charles Wadsworth, Shrewsbury, all of Mass.

[73] Assignee: Genzyme Corporation, Framingham, Mass.

[21] Appl. No.: 409,874

[22] Filed: Mar. 24, 1995

[51] Int. Cl.$^6$ .......................... A61K 48/00; C12N 15/00; C12N 5/00
[52] U.S. Cl. .................. 424/93.21; 424/93.2; 435/172.3; 435/240.1; 435/240.2; 435/320.1; 514/44
[58] Field of Search .................. 514/44, 2; 435/235.1, 435/172.1, 172.3, 240.1, 240.2, 91.1; 424/93.2, 93.21

[56] References Cited

FOREIGN PATENT DOCUMENTS

| | | |
|---|---|---|
| WO9412649 | 12/1993 | WIPO . |
| 9424297 | 10/1994 | WIPO . |
| 9502697 | 1/1995 | WIPO . |
| WO9511984 | 5/1995 | WIPO . |

OTHER PUBLICATIONS

Zabner et al., Gene Therapy 3:458–465, 1996.
Armentano et al., Human Gene Therapy 6:1343–1353, 1995.
Krougliak et al., Human Gene Therapy 6:1575–1586, 1995.
Welsh et al., Human Gene Therapy 6:205–218, 1995.
Wadsworth et al., J. Cell Biochem. Supp. 21A, Abstract No. c6–450, 1995.
Setoguchi et al., Blood 84:2946–2953, 1994.
Engelhardt et al., Human Gene Therapy 5:1217–1229, 1994.
Armentano et al., J. Cell Biochem. Supp. 18A, Abstract no. DZ 102, 1994.
Wilkinson et al., Nucleic Acids Res. 20:2233–2239, 1992.
Rosenfeld et al., Cell 68:143–155, 1992.
Jolly, D., Cancer Gene Therapy 1:51–64, 1994.
Marshall, Science: 269:1050–1055, 1995.
Neve, Trends in Neuroscience 16(7):251–253, 1993.
Berkner, BioTechniques 6(7):616–629, 1988.
NIH, "Report and Recommendations...", Dec. 7, 1995, pp. 1–40.
Vincent et al., Nature Genetics 5:130–134, 1993.
Descamps et al., Human Gene Therapy 5:979–985, 1994.
Stratford–Perricaudet et al., Human Gene Therapy 1:241–256, 1990.
Mitani et al., Human Gene Therapy 5:941–948, 1994.
Haddada et al., Human Gene Therapy 4:703–711, 1993.
Jaffe et al., Nature Genetics 1:372–378, 1992.
Zabner, J. et al., Nature Genetics 6:75–83, 1994.
Rich, D. et al., Human Gene Therapy 4:461–476, 1993.
Zabner, J. et al., Cell 75:207–216, 1993.
Crystal, R.G. et al., Nature Genetics 8:42–51, 1994.
Bridge, E. et al., J. Virol. 63:631–638, 1989.
Huang, M. et al., J. Virol. 63:2605–2615, 1989.
Klessig, D. et al., Mol. Cell. Biol. 4:1354–1362, 1984.
Weinberg, D. et al., Proc. Natl. Acad. Sci. USA 80:5383–5386, 1983.

*Primary Examiner*—Jacqueline M. Stone
*Assistant Examiner*—Andrew Milne
*Attorney, Agent, or Firm*—Brumbaugh, Graves, Donohue & Raymond

[57] ABSTRACT

The present invention relates to novel adenovirus vectors for use in gene therapy which are designed to prevent the generation of replication-competent adenovirus (RCA) during in vitro propagation and clinical use. The invention also provides methods for the production of the novel virus vectors. These vectors maximize safety for clinical applications in which adenovirus vectors are used to transfer genes into recipient cells for gene therapy.

8 Claims, 3 Drawing Sheets

E.C.= expresson cassette containing transgene of interest

ADENOVIRUS VECTORS FOR GENE THERAPY

The present invention relates to novel adenovirus vectors for use in gene therapy which are designed to prevent the generation of replication-competent adenovirus (RCA) during in vitro propagation and clinical use. The invention also provides methods for the production of the novel virus vectors. These vectors maximize safety for clinical applications in which adenovirus vectors are used to transfer genes into recipient cells for gene therapy.

BACKGROUND OF THE INVENTION

Prospects for gene therapy to correct genetic disease or to deliver therapeutic molecules depend on the development of gene transfer vehicles that can safely deliver exogenous nucleic acid to a recipient cell. To date, most efforts have focused on the use of virus-derived vectors that carry a heterologous gene (transgene) in order to exploit the natural ability of a virus to deliver genomic content to a target cell.

Most attempts to use viral vectors for gene therapy have relied on retrovirus vectors, chiefly because of their ability to integrate into the cellular genome. However, the disadvantages of retroviral vectors are becoming increasingly clear, including their tropism for dividing cells only, the possibility of insertional mutagenesis upon integration into the cell genome, decreased expression of the transgene over time, rapid inactivation by serum complement, and the possibility of generation of replication-competent retroviruses (Jolly, D., *Cancer Gene Therapy* 1:51–64, 1994; Hodgson, C. P., *Bio Technology* 13:222–225, 1995).

Adenovirus is a nuclear DNA virus with a genome of about 36 kb, which has been well-characterized through studies in classical genetics and molecular biology (Horwitz, M. S., "Adenoviridae and Their Replication," in *Virology*, 2nd edition, Fields, B. N., et al., eds., Raven Press, New York, 1990). The genome is classified into early (known as E1–E4) and late (known as L1–L5) transcriptional units, referring to the generation of two temporal classes of viral proteins. The demarcation between these events is viral DNA replication.

Adenovirus-based vectors offer several unique advantages, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39–66, 1992; Jolly, D., *Cancer Gene Therapy* 1:51–64, 1994). The cloning capacity of an adenovirus vector is about 8 kb, resulting from the deletion of certain regions of the virus genome dispensable for virus growth, e.g., E3, deletions of regions whose function is restored in trans from a packaging cell line, e.g., E1, and its complementation by 293 cells (Graham, F. L., *J. Gen. Virol.* 36:59–72, 1977), as well as the upper limit for optimal packaging which is about 105%–108% of wild-type length.

Genes that have been expressed to date by adenoviral vectors include p53 (Wills et al., *Human Gene Therapy* 5:1079–188, 1994); dystrophin (Vincent et al., *Nature Genetics* 5:130–134, 1993; erythropoietin (Descamps et al., *Human Gene Therapy* 5:979–985, 1994; ornithine transcarbamylase (Stratford-Perricaudet et al., *Human Gene Therapy* 1:241–256, 1990); adenosine deaminase (Mitani et al., *Human Gene Therapy* 5:941–948, 1994); interleukin-2 (Haddada et al., *Human Gene Therapy* 4:703–711, 1993); and α1-antitrypsin (Jaffe et al., *Nature Genetics* 1:372–378, 1992).

The tropism of adenoviruses for cells of the respiratory tract has particular relevance to the use of adenovirus in gene therapy for cystic fibrosis (CF), which is the most common autosomal recessive disease in Caucasians, that causes pulmonary dysfunction because of mutations in the transmembrane conductance regulator (CFTR) gene that disturb the cAMP-regulated Cl⁻ channel in airway epithelia (Zabner, J. et al., *Nature Genetics* 6:75–83, 1994). Adenovirus vectors engineered to carry the CFTR gene have been developed (Rich, D. et al., *Human Gene Therapy* 4:461–476, 1993) and studies have shown the ability of these vectors to deliver CFTR to nasal epithelia of CF patients (Zabner, J. et al., *Cell* 75:207–216, 1993), the airway epithelia of cotton rats and primates (Zabner, J. et al., *Nature Genetics* 6:75–83, 1994), and the respiratory epithelium of CF patients (Crystal, R. G. et al., *Nature Genetics* 8:42–51, 1994).

One of the critical issues remaining in the development of safe viral vectors is to prevent the generation of replication-competent virus during vector production in a packaging cell line or during gene therapy treatment of an individual. The generation of these replication competent viruses poses the threat of an unintended virus infection with attendant pathological consequences for the patient.

The presence of wild-type adenovirus in the recipient cells of human candidates for gene therapy presents a possibility for generating replication-competent adenovirus (RCA) due to homologous DNA sequences present in the vector and the recipient cells (Jolly, D., *Cancer Gene Therapy* 1:51–64, 1994). Furthermore, the generation of new viruses carrying a transgene may interfere with dosage requirements for optimal gene therapy as extra copies of the gene may be produced by new viruses carrying the transgene. It is therefore critical to develop vectors that are not only replication-defective, but are designed to minimize recombinogenic potential as well limit the harmful effects of a recombination event by self-destruction.

SUMMARY OF THE INVENTION

This invention provides for gene therapy vectors that are effective to deliver useful genes to patients and which are constructed to minimize toxic or immunologic consequences to the patient.

The invention is directed to novel adenovirus vectors which are inactivated by the occurrence of a recombination event within a packaging cell or a recipient cell and therefore prevent the generation of replication-competent adenovirus (RCA). The inactivation may occur through the loss of an essential gene, or by the generation of a vector genome that cannot be packaged.

The invention is also directed to vectors which minimize the occurrence of a recombination event with packaging cells or recipient cells by vector genome rearrangements that decrease homology with viral sequences that may be present in a packaging cell or a recipient cell in order to prevent the generation of RCA.

These vector designs increase the safety of recombinant adenovirus vectors for use as gene transfer vehicles in gene therapy applications.

Thus, in one aspect, the invention provides a nucleotide sequence which contains elements of an adenovirus genome as well as a heterologous gene of mammalian origin that is under the control of a eucaryotic transcriptional promoter. This nucleotide sequence is capable of functioning as a vector which allows expression of the aforementioned heterologous gene when the vector is placed in a cell of an individual. The said nucleotide sequence is further characterized by the absence from the sequence of a first element of the adenovirus genome that is essential to replication or packaging of the adenovirus in a host mammalian cell and the placement of a second element of the adenovirus genome that is itself essential to the replication or packaging of adenovirus in a host mammalian cell into the nucleotide sequence at, or directly adjacent to, the location the nucleotide sequence otherwise occupied by the first element.

An additional aspect of the invention is a nucleotide sequence where the first element is the E1a–E1b region of adenovirus genome and the second element may be any one of the E4 region of adenovirus, the region E2A, the gene encoding terminal protein or adenovirus structural proteins, such as fiber L5.

A still further aspect provides a nucleotide sequence containing elements of an adenovirus genome and a heterologous gene of mammalian origin that is under the control of a eucaryotic transcriptional promoter, in which the E1a–E1b region of the adenovirus genome is absent and where a stuffer sequence has been inserted into the nucleotide sequence in a location other than that of the heterologous gene of mammalian origin. A vector containing this sequence is further characterized in that legitimate recombination of the sequence with an element that is present in a helper cell used to replicate or package the sequence, or with an element that is present in a cell of an individual, and having homology with the E1a–E1b region, leads to the production of a lengthened nucleotide sequence that is substantially less efficient than an unmodified nucleotide sequence at being packaged in the helper cell or in a cell of said individual.

The invention also provides for a nucleotide sequence, as above, that includes the gene for adenoviral protein IX and a heterologous gene of mammalian origin that is under the control of a eucaryotic transcriptional promoter. This latter nucleotide sequence is characterized in that the E1a–E1b region of the adenovirus genome is absent and the gene that encodes protein IX has been repositioned to a location that deviates from its normal location in the wild-type adenovirus genome.

The invention also provides for a method for minimizing exposure of an individual undergoing gene therapy, using a virus vector to deliver a heterologous gene, to replication-competent virus comprising the step of treating said individual with a gene therapy composition that itself comprises a pharmaceutically acceptable carrier, and vectors using the nucleotide sequences described above.

DETAILED DESCRIPTION OF THE INVENTION

Figure 1:
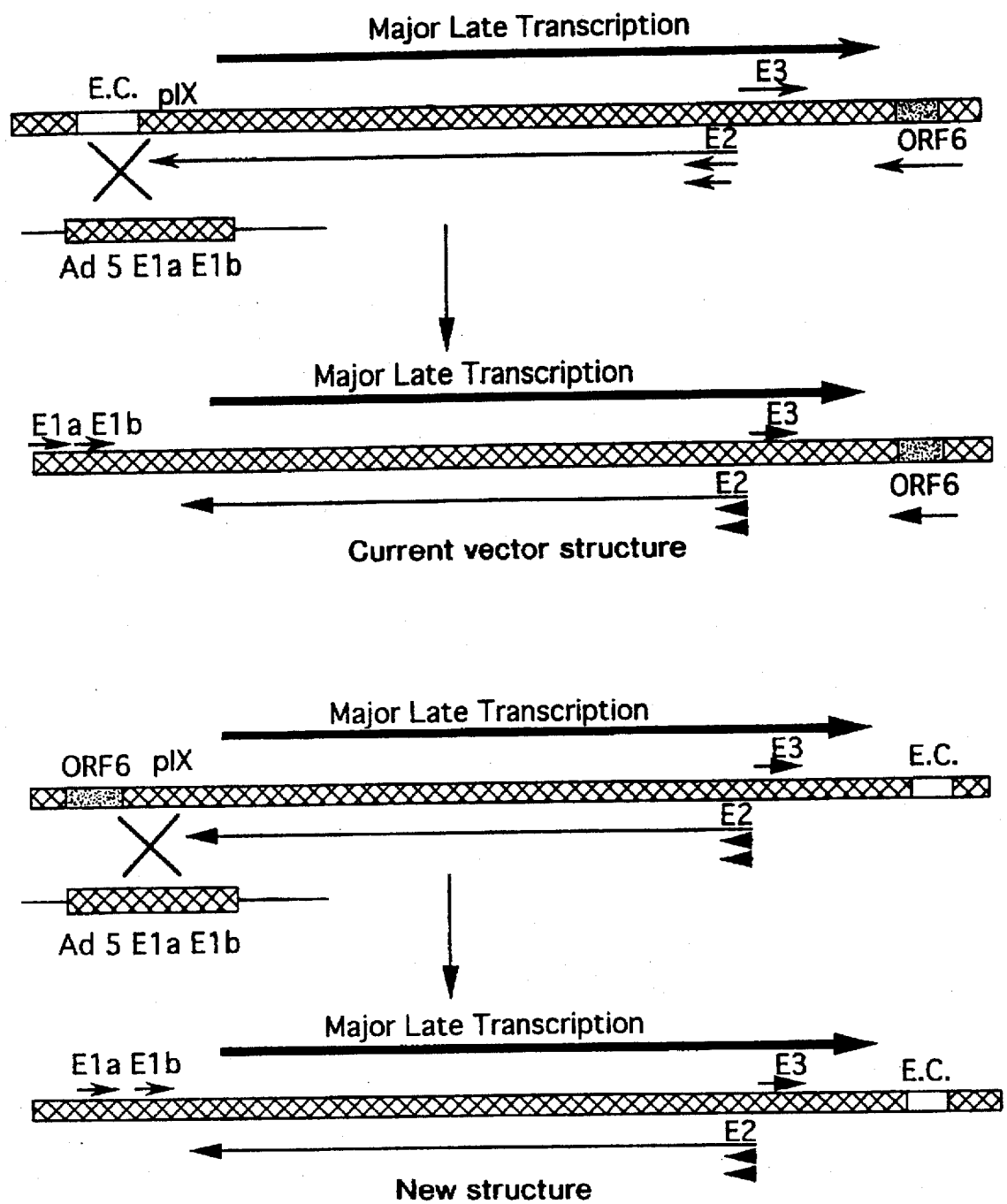
FIG. 1 Schematic diagram of current vector constructs, and the depiction of a recombination event in 293 cells. New constructs are depicted that produce a replication-incompetent vector by the deletion of an essential gene following recombination.

The invention is directed to adenovirus vectors which are inactivated by the occurrence of a legitimate recombination event within a packaging cell or a recipient cell and therefore prevent the generation of replication-competent adenovirus (RCA). Legitimate recombination is that which is dependent on specific and normal base pairing at sequences recognized as having homology for each other. The inactivation may occur through the loss of an essential gene, or by the generation of a vector genome that cannot be packaged.

The invention is also directed to vectors which minimize the occurrence of a recombination event with packaging cells or recipient cells by vector genome rearrangements that decrease homology with viral sequences that may be present in a packaging cell or a recipient cell to prevent the generation of RCA. Recipient cells targeted for gene therapy may contain wild-type adenovirus DNA sequence that can recombine with an adenovirus vector (Jolly, D., Cancer Gene Therapy 1:51–64, 1994).

These vector designs therefore increase the safety of recombinant adenovirus vectors for use as gene transfer vehicles in gene therapy applications.

Thus, in one aspect, the invention provides a nucleotide sequence which contains elements of an adenovirus genome as well as a heterologous gene of mammalian origin that is under the control of a eucaryotic transcriptional promoter. This nucleotide sequence is capable of functioning as a vector which allows expression of the aforementioned heterologous gene when the vector is placed in a cell of an individual. The nucleotide sequence is further characterized by the absence from the sequence of a first element of the adenovirus genome that is essential to replication or packaging of the adenovirus in a host mammalian cell and the placement of a second element of the adenovirus genome that is itself essential to the replication or packaging of adenovirus in a host mammalian cell into the nucleotide sequence at, or directly adjacent to, the location the nucleotide sequence otherwise occupied by the first element.

It is understood according to the practice of the invention that the reference to elements of the viral genome (such as first and second elements, referred to herein) that are termed essential includes also reference to elements that facilitate replication or packaging but which are not absolutely essential to such processes.

With respect to this aspect of the invention, the heterologous gene is any gene which is recognized as useful. Representative examples include genes of mammalian origin encoding, for example, proteins or useful RNAs; viral proteins such as herpes thymidine kinase, and bacterial cholera toxin for cytotoxic therapy.

An additional aspect of the invention is a nucleotide sequence where the first element is the E1a–E1b region of adenovirus genome and the second element may be any one of the E4 region of adenovirus, the region E2A, the gene encoding terminal protein or adenovirus structural proteins, such as fiber L5.

A still further aspect provides a nucleotide sequence containing elements of an adenovirus genome and a heterologous gene of mammalian origin that is under the control of a eucaryotic transcriptional promoter, in which the E1a–E1b region of the adenovirus genome is absent and where a stuffer sequence has been inserted into the nucleotide sequence in a location other than that of the heterologous gene of mammalian origin. A vector containing this sequence is further characterized in that legitimate recombination of the sequence with an element that is present in a helper cell used to replicate or package the sequence, or with an element that is present in a cell of an individual, and having homology with the E1a–E1b region, leads to the production of a lengthened nucleotide sequence that is substantially less efficient than an unmodified nucleotide sequence at being packaged in the helper cell or in a cell of said individual.

By additional sequence it is meant an inert sequence which does not affect adversely the function of the vector. The length of the additional sequence is selected based on the length of the sequence deleted. For example, if the deletion consists of the E1 region, an acceptable insert is about 3 kb, which is based on principles known by those skilled in the art, based on consideration of vector length for optimal packaging.

The invention also provides for a nucleotide sequence, as above, that includes the gene for adenoviral protein IX and a heterologous gene of mammalian origin that is under the control of a eucaryotic transcriptional promoter. This latter nucleotide sequence is characterized in that the E1a–E1b region of the adenovirus genome is absent and the gene that encodes protein IX has been repositioned to a location that deviates from its normal location in the wild-type adenovirus genome.

Preferably, it is repositioned to a location of generally at least about 100 nucleotides removed, preferably about 500 nucleotides removed, and most preferably, about 10,000 nucleotides removed.

The invention also provides for a method for minimizing exposure of an individual undergoing gene therapy, using a virus vector to deliver a heterologous gene, to replication-competent virus comprising the step of treating said individual with a gene therapy composition that itself comprises a pharmaceutically acceptable carrier, and vectors using the nucleotide sequences described above.

Recombination-Dependent Target Sequence Deletion Vectors

This aspect of the invention relates to vectors that prevent the generation of RCA by an adenovirus vector design in which an essential gene or genomic segment (the deletion target) is placed within a region that is potentially subject to recombination because a packaging cell or recipient cell contains homologous viral sequences. The result of a potential recombination event between cellular sequences and the vector is that this essential gene or genomic segment is deleted upon recombination, thereby rendering the viral vector replication-incompetent. This is accomplished by rearranging the genome so that the deletion target is moved from its original genomic location to be located within the region potentially subject to recombination. Although recombination may restore a missing viral sequence, the virus will be impaired by the loss of an essential gene that is caused by the recombination event.

In one embodiment of the invention, this vector design is applicable to preventing recombination events in a packaging cell line, such as 293 cells (Graham, F. L., *J. Gen. Virol.* 36:59–72, 1977). These cells, which contain an intact contiguous viral E1 DNA sequence derived from adenovirus 5 from the 5' ITR to about nucleotide 4300 (ref. for numbering is Roberts, R. J., in *Adenovirus DNA*, Oberfler, W., ed., Matinus Nihoft Publishing, Boston, 1986) integrated into the genome, are able to supply the E1 gene products in trans to an E1-deleted adenovirus vector. The generation of RCA is possible from recombination between the E1 sequences in the cell and the remaining sequences at the boundary of E1 in the vector, such as protein IX, if enough flanking homologous sequence is present to facilitate a legitimate recombination event.

In a specific embodiment, an adenovirus vector deleted for the E1 region and the E4 region except for the ORF6 gene is constructed by inserting an expression cassette into the E4-deleted region. (FIG. 1). The ORF6 gene is moved to the E1-deleted region. The E4 region of an adenovirus vector may be deleted except for ORF6 due to its role in DNA replication, late mRNA accumulation, and shutoff of host protein synthesis (Bridge, E. et al., *J. Virol.* 63:631–638, 1989; Huang, M. et al., *J. Virol.* 63:2605–2615, 1989). If a recombination event occurs between the viral sequences and 293 cells, the E1 sequences are gained and the ORF6 gene is deleted, such that the vector is still replication-defective.

In a further aspect of the invention, a vector may be customized to prevent the generation of RCA from any packaging cell line. The deletion target gene or segment will be engineered into the region of the vector which has homology with the DNA contained in the packaging cell line. Thus, recombination within this region will cause the target gene or segment to be deleted, resulting in the generation of replication-incompetent viral vectors. Vectors in which the deletion target is inserted into the E2 or E4 regions, for example, may be designed to circumvent recombination events in packaging cell lines that supply E2 or E4 gene products (Klessig, D. et al., *Mol. Cell. Biol.* 4:1354–1362, 1984; Weinberg, D. et al., *PNAS* 80:5383–5386, 1983). Analogous constructs designed to circumvent recombination in analogous packaging cell lines are within the scope of the invention.

In a further embodiment of this invention, this vector design can be used to preclude the formation of RCA from recombination with wild-type adenovirus that may be present in a patient's cell. The presence of wild-type adenovirus in human candidates for adenovirus-based gene therapy may present a source of viral DNA sequences for recombination events that generate RCA from a replication-incompetent adenovirus vector (Jolly, D., *Cancer Gene Therapy* 1:51–64, 1994). Prevention of RCA production may be accomplished by placing essential genes or segments within one or more regions in the vector that may potentially be subject to recombination with the wild-type adenovirus. By placing essential targets in potential sites for recombination, one or more recombination events will serve to delete essential viral genes, and thereby render the viral vector replication-incompetent.

Figure 2:
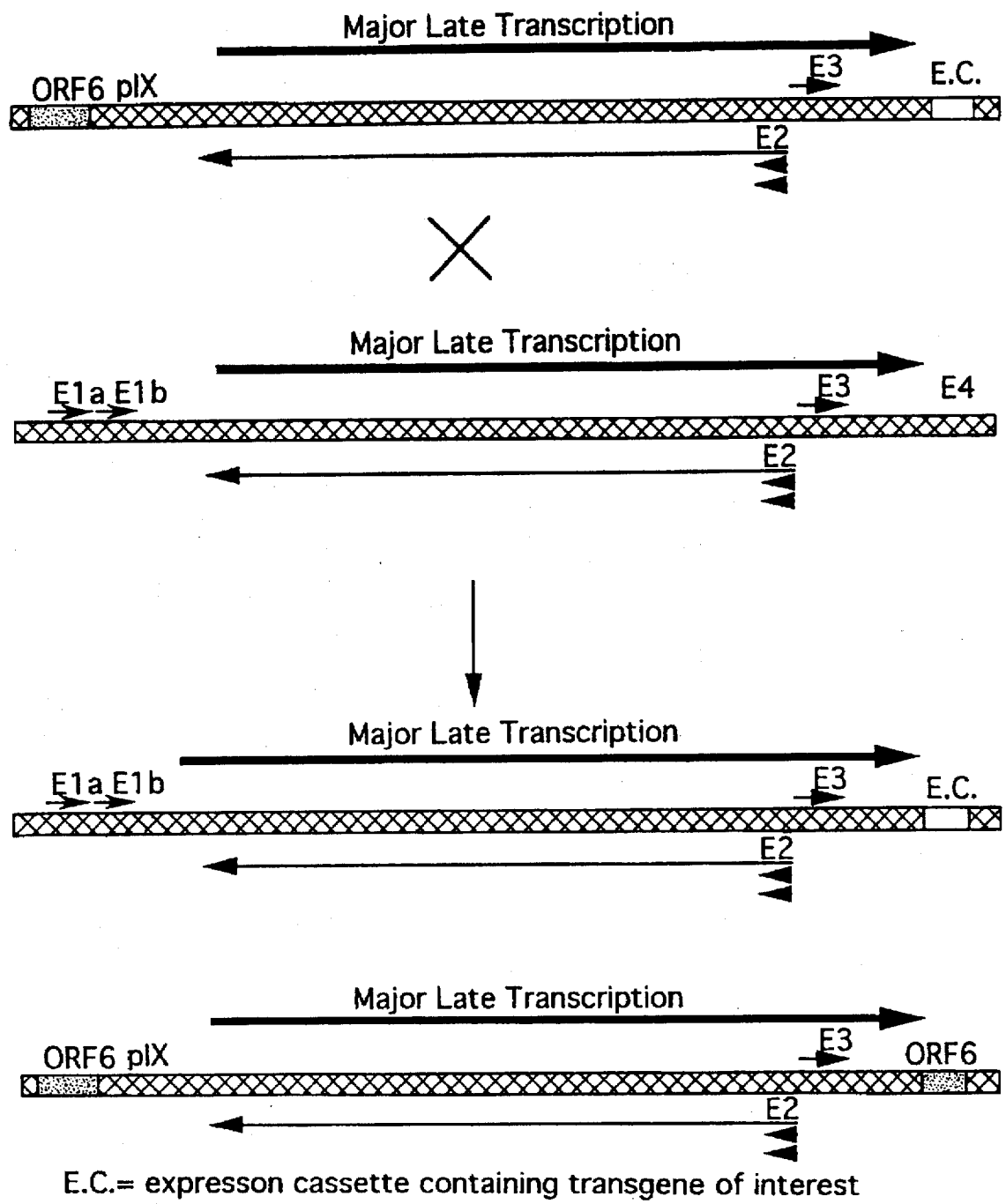
FIG. 2 A novel vector of the invention is depicted which, upon recombination with wild-type virus, produces replication-incompetent vectors deleted for an essential gene or segment.

In another embodiment, depicted in FIG. 2, a vector is constructed that upon recombination with wild-type virus, is rendered replication-incompetent. The vector contains the ORF6 gene positioned in the deleted E1 region, and an expression cassette inserted into the deleted E4 region. The central portion of the vector genome is homologous to wild-type adenovirus, and upon a recombination event, the vectors genomes so generated will be replication-incompetent as depicted in FIG. 2.

Essential adenovirus genes or genomic segments which may be positioned to serve as targets for deletion upon a recombination event include ORF6, L5 (fiber protein), the entire E4 region, the E2A region, terminal protein, or any other essential viral genes or segments.

Recombination-Dependent Packaging-Defective Vectors

This aspect of the invention relates to vectors that are rendered packaging-defective upon the occurrence of a recombination event with a packaging cell or a recipient cell, preventing the generation of RCA. This design takes advantage of limitations that exist on the genome length that can be packaged into an adenovirus virion. The size of an adenovirus genome that can be optimally packaged into new virions may exceed its wild-type length up to about 105%–108% and still be packaged into new virions (Berkner, K. L., Curr. Top. Micro. Immunol. 158:39–66, 1992). If a recombination event generates a virus genome that exceeds the packaging limit, it will not be packaged and RCA are not generated.

Vectors that are packaging-defective following recombination can be created by engineering the vector DNA such that its length is at least 101% of the wild-type length. This can be accomplished even with vectors that contain deletions of the wild-type adenoviral genome because of the insertion of a heterologous DNA sequence that compensates for the deletion and maintains the genome at near-wild-type length.

The heterologous DNA sequence may solely code for a gene of interest, or alternatively, where a heterologous gene is at small size, additional heterologous stuffer DNA sequence may be added so as to render the vector genome at a size of at least 101% of wild-type length. Stuffer is a term generally recognized in the art intended to define functionally inert sequence intended to extend the length, thereof, such as certain portions of bacteriophage lambda.

In another embodiment of this aspect of the invention, a vector is designed in which the E1 region is deleted as well as the E4 region except for the ORF6 gene, for a total deletion of 5 kb, and the CFTR gene is inserted into the E4 deletion region. This vector size is 101.3% of wild-type length. Following an E1-mediated recombination event in 293 cells, for example, that inserts the E1 region into the vector, the genome will increase to about 108% of wild-type length, rendering it packaging-defective and preventing the generation of RCA.

It will be understood by those skilled in the art that the concept of recombination-dependent packaging-defective adenovirus vectors may be practiced by using any number of viral or non-viral DNA fragments that are engineered into any number of sites in the vector, with an overall goal of maintaining a vector size that will exceed optimal packaging length upon recombination.

Scrambled Genome Vectors That Minimize Recombination And Generation Of RCA By Recombination In this aspect of the invention, the vector genome derived from wild-type adenovirus is rearranged so as to perturb the linear arrangement of the viral coding regions. In one embodiment, this "scrambling" of the genome reduces the potential for recombination between a wild-type adenovirus that may be found in a human candidate for gene therapy and the adenovirus vector. This reduction is due to the fact that long stretches of homologous DNA sequences between the cell and vector are eliminated when the viral sequences in the vector are rearranged. The likelihood of recombination is reduced as the homologous regions are reduced in length. In this manner, the generation of RCA is minimized. Regions of the adenovirus genome which may be scrambled included, for example, the E2A region, the E4 region, ORF6, L5 (fiber protein), terminal protein, or any combination of these and other regions of the viral genome which result in a scrambled genome whose linear sequence deviates from wild-type.

This concept may be applied to vectors where more than one region of the adenovirus is deleted, such that restoration of replication-competence requires several recombination events, each of which is rendered less likely as the linear homology between the vector and cell is reduced by scrambling.

This concept may be analogously applied to minimizing recombination between an adenovirus vector and a packaging cell line, by designing the vector so that stretches of homology with the cell line are perturbed by rearrangement, reducing their effective length and the likelihood of recombination. In one example of this embodiment of the invention, the potential for recombination between an adenovirus vector and 293 cells is decreased by rearranging the protein IX sequences in the vector. The protein IX sequences are often found at the right-hand boundary of the deleted E1 region in a vector. Protein IX sequences are also contained within 293 cells at the boundary of the E1 adenovirus insert, and may facilitate recombination between the vector and cellular sequences. The result is that restoration of E1 sequences to the vector may occur by a protein IX-mediated recombination event. The relocation or mutagenesis of a protein IX boundary from the E1 deletion region in a vector will decrease the likelihood of such an event, and of the generation of RCA. Such a vector is described in Example 1, infra, and FIG. 3.

Parameters Of The Vectors

The adenovirus vectors of the invention may be derived from the genome of various adenovirus serotypes, including but not limited to, adenovirus 2, 4, 5, and 7, and in general, non-oncogenic serotypes.

The adenovirus vectors of the invention may be engineered to carry any heterologous gene for delivery and expression to a target cell. The gene may be engineered into various sites within the vectors, including but not limited to, the E1 region, the E2 region, the E3 region and the E4 region, using techniques that are well known to those skilled in the art (Current Protocols in Molecular Biology, Ausubel, F. et al., eds., Wiley and Sons, New York, 1995). The heterologous gene cloned into the adenovirus vector may be engineered as a complete transcriptional unit, including a suitable promoter and polyadylation signal. Such promoters including the adenovirus E1 promoter or E4 promoter, for example, as well as others including, but not limited to, the CMV promoter and the PGK promoter. Suitable polyadenylation signals at the 3' end of the heterologous gene include, but are not limited to, the BGH and SV40 polyadenylation signals. The E3 region of the adenovirus genome may be deleted in order to increase the cloning capacity of a vector, or it may be left in the vector construct, according to conditions encountered by one practicing the present invention. It is presently preferred to leave at least a substantial portion of the E3 region in the vector so as to minimize, in some aspects, immune response by the patient to the vector construct, including serious inflammatory consequences.

Genes that may be engineered into the adenovirus vectors of the invention include, but are not limited to, CFTR for CF, α1-antitrypsin for emphysema, soluble CD4 for AIDS, ADA for adenosine deaminase deficiency and any other genes that are recognized in the art as being useful for gene therapy.

The vectors of the present invention may have application in gene therapy for the treatment of diseases which require that a gene be transferred to recipient cells for the purpose of correction of a missing or defective gene, or for the purpose of providing a therapeutic molecule for treatment of a clinical condition.

The vectors of the present invention can be adapted to ex vivo and in vitro gene therapy applications.

It will be understood that the concepts of vector designs contained in the foregoing sections may analogously be applied to other viral vectors, including, but not limited to, retrovirus, herpes, adeno-associated virus, papovavirus, vaccinia, and other DNA and RNA viruses.

EXAMPLE

CONSTRUCTION OF A SCRAMBLED ADENOVIRUS VECTOR THAT PREVENTS PROTEIN IX-DEPENDENT RECOMBINATION

Figure 3:
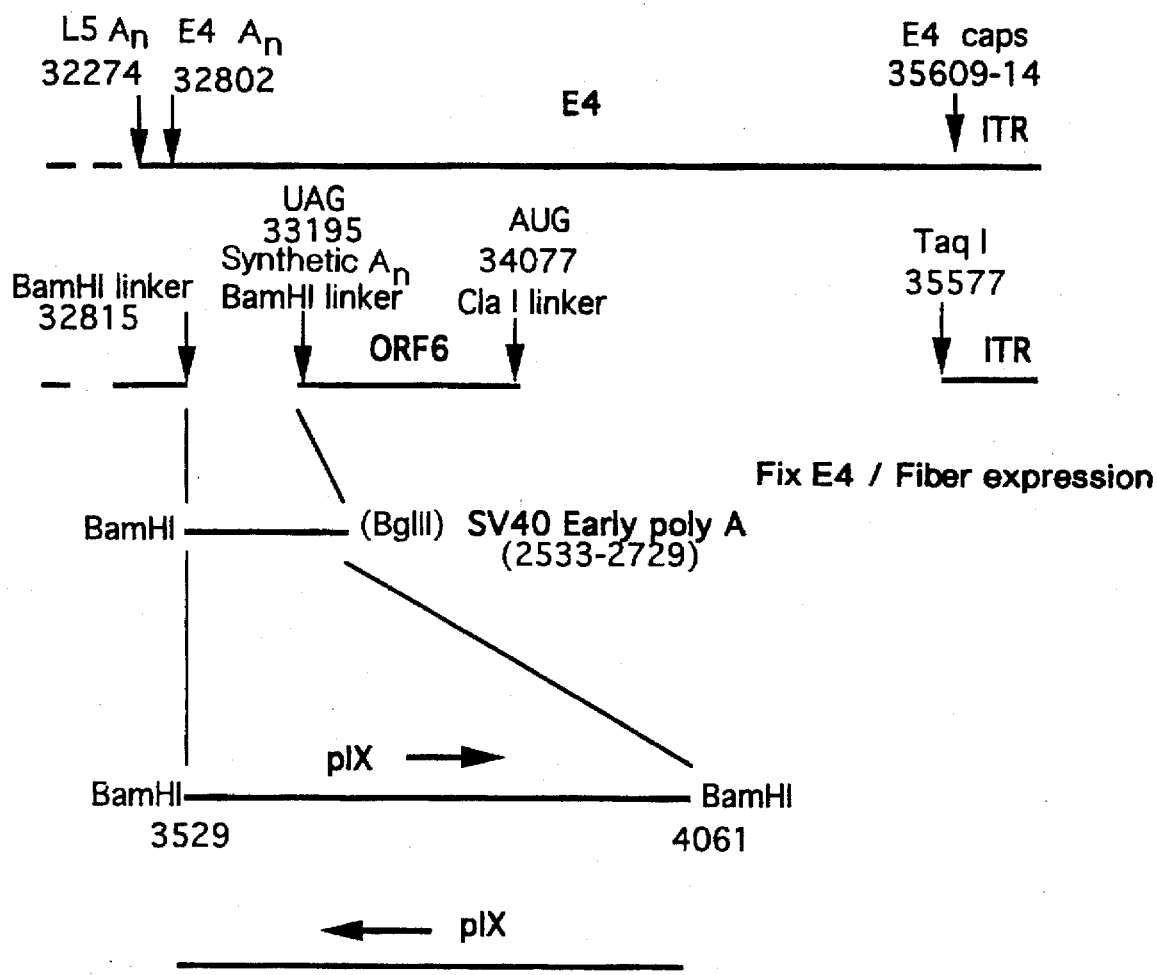
FIG. 3 The 3' end of a novel vector is depicted, in which protein IX is repositioned to the E4-deleted region so as to minimize recombination between a vector and 293 cells.

A novel adenovirus vector is constructed by starting with the plasmid Ad2E4ORF6 (PCT Publication Number WO 94/12649), deleted for E1 and in which E4 sequences are deleted from the ClaI site at 34077 to the TaqI site at 35597. The ORF6 sequence from 33178 to 34082 is inserted into the E4 region. The SV40 early polyA sequence is inserted adjacent to the ORF6, which also serves to prevent readthrough from the ORF6 gene into the L5 (fiber) sequences. Protein IX is repositioned from its original location in the virus genome into the E4-deleted region as a Bam HI fragment. The protein IX fragment contains its own promoter, and may be cloned into the vector in either direction. The construct is shown in FIG. 3. The plasmid is transfected into 293 packaging cells to produce a vector stock using standard techniques (*Current Protocols in Molecular Biology*, Ausubel, F., et al., eds., Wiley & Sons, 1995). The resulting vector is less susceptible to a recombination event with viral sequences in 293 cells due to the repositioning of the protein IX gene, which decreases homology between the vector and the 293 cell.

We claim:

1. A recombinant adenovirus vector having a deleted E1 region of the adenovirus genome, into which a heterologous gene has been inserted, and in which the protein IX gene has been relocated in the adenovirus genome to a location thereof other than the location in which said protein IX gene normally resides, such that generation of replication-competent adenoviruses is minimized or eliminated.

2. The vector of claim 1 in which one or more open reading frames of the E4 region is deleted.

3. The vector of claim 2, in which the protein IX gene is relocated to the E4 region.

4. The vector of claim 2, in which ORF6 of the E4 region is retained.

5. The vector of claim 4, in which the protein IX gene is inserted adjacent to the ORF6 gene.

6. The vector of claim 1, in which the heterologous gene is a gene encoding CFTR.

7. The vector of claim 1 in which the heterologous gene is operably linked to a eucaryotic promoter, so as to allow for expression of the gene.

8. The vector of claim 1, in which the adenovirus is selected from among adenovirus serotypes 2, 4, 5 and 7.

* * * * *